United States Patent [19]

Hall

[11] 4,047,524
[45] Sept. 13, 1977

[54] SURGICAL IMPLANT SPINAL STAPLE

[75] Inventor: John Emmett Hall, Boston, Mass.

[73] Assignee: Downs Surgical Limited, Mitcham, England

[21] Appl. No.: 680,233

[22] Filed: Apr. 26, 1976

[30] Foreign Application Priority Data

Apr. 28, 1975  United Kingdom .............. 17611/75

[51] Int. Cl.² .......................... A61F 5/00; A61B 17/18
[52] U.S. Cl. ........................................ 128/69; 128/78; 128/92 B; 128/92 D; 85/49
[58] Field of Search ................. 128/92 R, 92 B, 92 D, 128/78, 69; 85/49

[56] References Cited

U.S. PATENT DOCUMENTS

| | | | |
|---|---|---|---|
| 2,489,870 | 11/1949 | Dzus ................................. | 128/92 B |
| 3,693,616 | 9/1972 | Roaf et al. .............................. | 128/69 |

OTHER PUBLICATIONS

Mario M. Stone Table Staple, Richards Mfg. Co. Orthopedic and Instruments (catalog), Memphis Tenn., 1966, p. 115.

Mario M. Stone Table Staple, Orthopedic Catalog, Richards Mfg. Co., Inc., Memphis Tenn., Copyright 1974, Effective Price List of Nov. 15, 1974, p. 72.

"A New Surgical Approach for Correcting the Scoliotic Spine Using a Tensioned Cable Secured to the Convex Curve of the Affective Vertebrae" by A. F. Dwyer, Advertisement p. 57, The Journal of Bone & Joint Surgery, vol. 53A, No. 2, Mar. 1971.

*Primary Examiner*—Ronald L. Frinks
*Attorney, Agent, or Firm*—Haight & Huard

[57] ABSTRACT

Surgical implant, known as a double-hole spinal staple for use in securing metal cables to vertebrae in operations for the correction of scoliosis.

6 Claims, 5 Drawing Figures

SURGICAL IMPLANT SPINAL STAPLE

This invention relates to a surgical implant for use in the correction of curvature of the spinal column.

One technique that is used for the correction of spinal curvatures is the Dwyer technique of anterior instrumentation of the spine; (c.f. A. F. Dwyer, "Anterior approach to scoliosis", *Journal of the Western Pacific Orthopaedic Association*, Vol. VI, No. 1, March 1969; A. F. Dwyer et al., "Anterior approach to scoliosis," *Clinical Orthopaedics and Related Research*, No. 62, pp. 192-202, 1969; and A. F. Dwyer, "Anterior approach to scoliosis", ibid, No. 93, July 1973). This technique involves operation on the front of the spine, with access to the spine being gained by the removal of one rib, or possibly of two ribs. This method may be used for the correction of scoliosis (lateral curvature of the spinal column) when posterior elements are absent, such as in myelomeningocele or after an extensive laminectomy. It is particularly useful when lordosis (curvature of the spinal column with a forward convexity) is associated with scoliosis, and can often be used as a supplementary means of fixation in very long paralytic curves, especially those associated with lordosis in the lumbar region.

The technique involves the application of compression on the convex side of the spinal curve, after the contents of the discs have been excised, so as to straighten the curve. The compression is applied by means of a metal cable threaded through the heads of screws, one of which is anchored through a metal staple in each vertebra.

A staple or "saddle" of such a size as to fit snugly over the vertebra is first selected and driven into place over the vertebra. A screw is then passed through a hole in the staple and into the vertebra until only the head of the screw protrudes above the staple. A metal cable is passed through a hole in the head of the screw. The procedure is repeated on successive vertebrae with a single cable being passed through all screw heads. Tension is applied to the cable, to obtain the necessary corrective force, by means of a special tensioner. The tension may be applied one stage at a time, after the cable has been passed through each respective screwhead, or it may be applied after the cable has been passed through several or all of the screw-heads. When the correct tension has been obtained the screw-head is crimped over the cable so as to maintain the cable at the necessary tension.

In carrying out this technique, one normally works from the top part of the spine to be corrected downward, as this generally enables the final correction to be made at the most accessible level of spine, namely in the region of the lumbar vertebrae. If one were to work from the lumbar vertebrae upward to the thoracic vertebrae, instrumentation would be very difficult—the top screws would be difficult to apply and the tensioner would be awkward to use. When working from the top downward, however, difficulty occurs if instrumentation has to be continued down to the lumbo-sacral level, as is usually necessary when dealing with the paralytic curve or a curve associated with myelomeningocele. In these lower regions of the spine, it again becomes extremely awkward to use the tensioner, and moreover, the screws and staples cannot conveniently be used on the sacral vertebrae.

The complete specification accompanying U.K. Patent Application No. 17610/75, describes and claims an implant, which may be referred to as a sacral anchor, by means of which these difficulties in reaching the sacrum can be overcome. This sacral anchor is used to fix the lower end of the cable to the sacrum. It is generally inserted over the body of sacral vertabra S1 and into the disc space S1/S2. Instrumentation is then carried out beginning at this level and continuing upward to the lumbar vertebrae. If, however, instrumentation were to be continued further upward to the thoracic vertebra, the previously mentioned dfficulties would again occur.

The present invention provides a surgical implant, which is of metal, is substantially U-shaped, and has two substantially parallel laminar legs for insertion one above and one below a vertebra, the two legs being joined by a laminar bridge portion having two holes, each to accommodate a spinal screw, with the line joining the centres of the holes being inclined, in the plane of the bridge portion, with respect to the line joining the centres of the ends of the legs which are secured to the bridge portion.

This implant enables two cables to be used, thus overcoming the above-mentioned difficulties that occur when working at the lumbo-sacral level. One of the cables is fixed first at the top and then worked downward to the lumbar region, generally to lumbar vertebra L3, and the other is fixed first at the bottom by means of a sacral anchor as mentioned above and worked upward to the lumbar region, generally to lumbar vertebra L2. The final tension can then be applied, and thus the final correction obtained, at this, the most accessible, level of the spine.

In order for there to be sufficient support in the region in which the two cables meet it is necessary for there to be some overlap of the two cables, and this can be achieved by the use of the present surgical implant, which may be referred to as a double-hole spinal staple. This double-hole spinal staple permits the insertion of two screws into a single vertebra, one screw to receive one cable and the second screw to receive the second cable. Thus the required overlap of the cables is obtained.

In the situation described above, it is generally most convenient to use a double-hole spinal staple on each of the L2 and L3 lumbar vertebrae, with single hole staples being used in the usual manner on the other vertebrae. There may, however, be occasions when it is desired to use only one double-hole spinal staple or to use three or more, or when it is desired to use them on other vertebrae than those mentioned. The double-hole spinal staple simply permits the insertion of two screws into a single vertebra, which in turn permits the attachment of two cables to a single vertebra.

The staple has two substantially parallel and substantially laminar legs. In use, these should fit snugly either side of a vertebra, one above and one below the vertebra, and they may even be countersunk slightly into the vertebra. The end of each leg is advantageously so bevelled on its outer surface that the leg terminates in a wedge-shape; this aids in fixing and holding the staple in place over the vertebra.

The laminar bridge portion, which, in use, fits over the front of the vertebra is advantageously slightly convex in shape as viewed from the side of the bridge portion remote from the legs, as this enables the staple to be fitted more snugly over the vertebra. In order that this bridge portion may accommodate the two holes for the spinal screws, it advantageously has a width that is two to three times the width of each leg.

The thickness of the legs and of the bridge portion may suitably be substantially 1 mm. The distance between the insides of the two legs of the staple may be from 20 to 30 mm. For most purposes it is suitable to manufacture the staples in three different sizes of, for example, 22 mm, 25 mm, and 28 mm, as this generally gives an adequate choice to enable a suitably sized staple to be selected for any particular application. The actual size chosen for a particular application will depend on the size of the vertebra to which it is to be secured.

The staples can conveniently be manufactured by cutting a suitable shape from a sheet of metal and bending it to the desired shape. The metal used is normally titanium as this neither is adversely affected by, nor adversely affects, body tissue. Various double-hole spinal staples constructed in accordance with the invention will now be described, by way of example only, with reference to FIGS. 1 to 5 of the accompanying drawings, in which.

Figure 1:
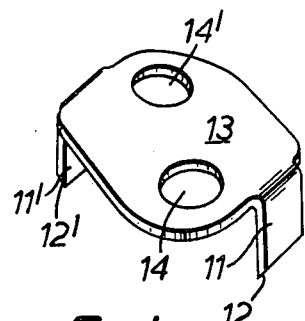
FIG. 1 is a perspective view of one form of a double-hole spinal staple.
Figure 2:
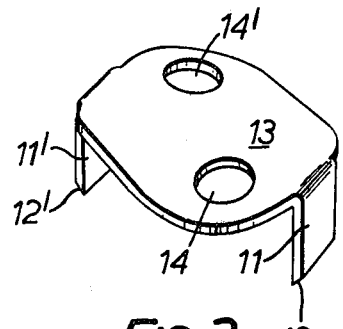
FIG. 2 is a perspective view of a second form of double-hole spinal staple.
Figure 3:
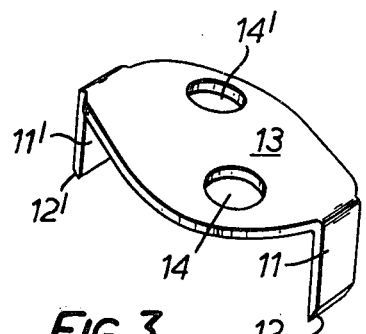
FIG. 3 is a perspective view of a third form of double-hole spinal staple.
Figure 4:
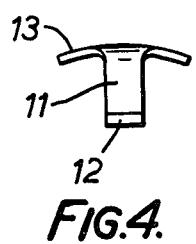
FIG. 4 is an end view of the staple of FIG. 1.

Each of the double-hole spinal staples of FIGS. 1, 2 and 3 is substantially U-shaped. Each has two substantially parallel laminar legs 11, 11' and each leg has a bevelled, wedge-shaped end 12, 12' respectively. The two legs are jointed by a laminar bridge portion 13 having two holes 14, 14', which are diagonally opposed in relation to the legs 11, 11'. The bridge portion 13 is slightly convex in shape as viewed from the side remote from the legs 11, 11', as can clearly be seen in FIG. 4. The three are all made of titanium about 1 mm thick. The distance between the inner surfaces of the legs 11, 11' is greater in the staple of FIG. 3 than in that of FIG. 2, and is smaller still in the staple of FIG. 1.

Figure 5:
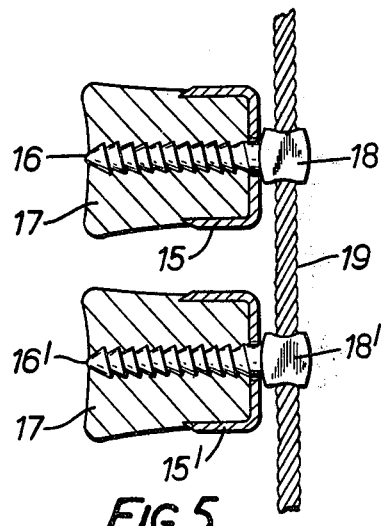
FIG. 5 is diagrammatic vertical cross-sectional view of two single-hole staples each secured to a vertebrae.

FIG. 5 of the accompanying drawings is a diagrammatic vertical cross-sectional view of two single-hole staples each secured to a vertebra. It is included merely to illustrate the manner in which spinal staples are used, and single-hole staples (not according to the invention) are shown for simplicity. Two single-hole spinal staples 15, 15' are snugly secured by spinal screws 16, 16' to vertebrae 17, 17'. Each screw has a head 18, 18' through which can be passed a titanium cable 19. The double-hole staples according to the invention can be snugly secured to the respective vertebra in an identical manner except that two spinal screws are used for each staple. When the double-hole staples have been secured to the vertebrae, a metal cable can be passed through the screw-heads, tension can be applied to the cable, and the screw-heads can be crimped over the cable, in the usual manner.

A special screw and nut for use in securing metal staples (single-hole or double-hole) to the vertebrae is described and claimed in the complete specification accompanying U.K. Patent Application No. 17612/75, and a special tensioner for applying the desired tension to the metal cable is described and claimed in the complete specification accompanying U.K. Patent Application No. 17613/75.

What I claim is:

1. A metal spinal staple substantially U-shaped in side view and capable of securing a pair of metal tensioning cables to a vertebra via spinal screws, which comprises:

a pair of substantially parallel, perpendicularly offset laminar legs having free ends which are bevelled on the outer surfaces to terminate in a wedge shape, the parallel distance between said legs being such as to fit snugly over either side of a vertebra;

an integral, substantially solid and rectangular laminar bridge portion extending perpendicularly between the diagonally opposed bases of said legs along its length, having a width greater than the width of each leg and having curved corners between said legs; and a pair of diagonally opposed spinal screw receiving apertures formed in said bridge portion proximate to said curved corners such that a line joining the centers of said apertures is inclined with respect to a line joining the centers of said legs in the plane of the bridge portion.

2. An implant as claimed in claim 1, wherein the bridge portion is slightly convex in shape as viewed from the side thereof remote from the legs.

3. An implant as claimed in claim 1, wherein the bridge portion has a width that is two to three times the width of each leg.

4. An implant as claimed in claim 1, wherein the legs and the bridge portion each have a thickness of substantially 1 mm.

5. An implant as claimed in claim 1, wherein the distance between the insides of the two legs is from 20 to 30 mm.

6. An implant as claimed in claim 1, which is made of titanium.

* * * * *